United States Patent

Byrom et al.

[11] Patent Number: 6,080,562
[45] Date of Patent: Jun. 27, 2000

[54] HV/HB COPOLYMER PRODUCTION

[75] Inventors: David Byrom, Middlesbrough, United Kingdom; Alexander Steinbuchel, Gottingen, Germany

[73] Assignee: Monsanto Company, St. Louis, Mo.

[21] Appl. No.: 07/949,524

[22] PCT Filed: May 24, 1991

[86] PCT No.: PCT/EP91/00978

§ 371 Date: Nov. 25, 1992

§ 102(e) Date: Nov. 25, 1992

[30] Foreign Application Priority Data

May 25, 1990 [GB] United Kingdom .................. 9011777

[51] Int. Cl.⁷ ................ C12P 7/62; C12N 1/38; C12N 1/20
[52] U.S. Cl. .............. 435/135; 435/244; 435/252.1; 435/829
[58] Field of Search .................. 435/135, 829, 435/244, 252.1

[56] References Cited

U.S. PATENT DOCUMENTS

| | | | |
|---|---|---|---|
| 4,477,654 | 10/1984 | Holmes et al. | 528/361 |
| 4,876,331 | 10/1989 | Doi | 528/361 |
| 4,997,909 | 3/1991 | Doi | 435/135 |
| 5,126,255 | 6/1992 | Anderson et al. | 435/135 |

FOREIGN PATENT DOCUMENTS

| | | |
|---|---|---|
| 204442 | 12/1986 | European Pat. Off. . |
| 288908 | 11/1988 | European Pat. Off. . |

*Primary Examiner*—Herbert J. Lilling
*Attorney, Agent, or Firm*—Jon H. Beusen, Esq.; Howrey Simon; Arnold & White LLP

[57] ABSTRACT

Microorganisms are modified to permit production of HV/HB copolymers from substrates such as glucose by inducing amiono acid overproduction in those capable of synthesising and polymerising hydroxybutyrate or adding to an amino acid overproducer the genetic material necessary for it to synthesise and polymerise hydroxybutrate.

9 Claims, No Drawings

HV/HB COPOLYMER PRODUCTION

This invention relates to a process for the production of HV/HB copolymers and for microorganisms for use in such a process.

Conventionally the production of a copolymer containing monomer units of both 3-hydroxybutyrate, herein denoted as HB, and 3-hydroxyvalerate, herein denoted as HV, requires the microorganism to be cultivated on a substrate containing propionic acid, or another compound from which the microorganism can synthesise the HV monomer units. Usually, the microorganism is unable to synthesise HV monomer units directly from glucose.

In copending European Patent Application No. 90304267.9 it has been shown that certain strains of the species Rhodococcus are able to synthesise both HV and HB monomer units from glucose, thereby producing and accumulating HV/HB copolymers.

We have discovered that those strains of the species Rhodococcus capable of producing, and accumulating, HV/HB copolymers have the characteristic that they overproduce at least one amino acid, specifically at least one of methionine and preferably isoieucine or valine, and that these overproduced amino acids are metabolised to propionyl CoA, and thence to the required HV monomer units.

It is also known that certain strains of specific species of the coryneform group of microorganisms, e.g. *Corynebacterium glutamicum*, are able to be used industrially to produce amino acids by fermentation.

We have found a general method for the preparation of microorganisms capable of producing, and accumulating, HV/HB copolymers which comprises providing within a suitable microorganism the ability to overproduce at least one of isoleucine, methionine and valine. Such microorganisms may then be used in a general microbiclogical process for the production of HV/HB copolymers, when provided with suitable substrate for example comprising glucose, or a compound metabolisable to glucose.

The invention comprises a method of producing a microorganism capable of sythesizing HV/HB copolymer when cultivated on a substrate containing a component from which the microorganism can synthesise both HV and HB monomer units from a first microorganism which is capable of metabolising the substrate to acetyl CoA and is also capable of degrading an amino acid selected from methionine, valine and isoleucine to propionyl CoA which method comprises when said first microorganism is capable of synthesising and polymerising HB monomer units when cultivated on said substrate but is not capable of amino acid overproduction, inducing overproduction of said amino acid in said first microorganism, and when said first microorganism is not capable of synthesising and polymerising HB monomer units when cultivated on said substrate but is capable of overproducing said amino acid, transferring to said first microorganism the genetic information necessary for it to synthesise and polymerise HB monomer units when cultivated on said substrate from a second microorganism, said second microorganism being capable of producing and accumulating HB homopolymer when cultivated on said substrate We also provide a method of producing a microorganism capable of synthesising HV/HB copolymer when cultivated on a substrate containing a component from which the microorganism can synthesise both HV and HB monomer units, said component being glucose, fructose, acetate, a lactate or ethanol or a substrate metabolisable thereto from a first microorganism which method comprises when said first microorganism is capable of synthesising and polymerising HB monomer units when cultivated on said substrate and degrading an amino acid to propionyl CoA, but is not capable of overproducing said amino acid selected from methionine valine and isoleucine, inducing overproduction of said amino acid in said first microorganism, and when said first microorganism is not capable of synthesising and polymerising HB monomer units when cultivated on said substrate but is capable of overproducing said amino acid and degrading it to propionyl CoA transferring to said first microorganism the genetic information necessary for it to synthesise and polymerise HB monomer units when cultivated on said substrate from a second microorganism which is capable of producing and accumulating HB homopolymer when cultivated on said substrate.

We further provide a general microbiological process for the production of HV/HB copolymer using a microorganism produced according to the above method, which process comprises cultivating said microorganism on a substrate comprising essentially of glucose, or a compound metabolisable to glucose.

Where the first microorganism is one which is capable of producing, and accumulating, HB copolymer the microorganism is preferably a strain of Alcaligenes. Examples of such strains are *Alcaligenes eutrophus* NCIMB 11599, and NICMB 40124. In particular, NCIMB 40124 is preferred in that in this strain the use of propionyl CoA for growth is blocked, thereby giving rise to improved efficiency of HV/HB copolymer production, and also higher percentages of HV monomer in the copolymer.

The method for preparing microorganisms in which amino acid overproduction is apparent may include exposure of the microorganism to amino acid analogues such as amino butyric acid, and norvaline. The required mutations may be spontaneous, or may be induced by the use of suitable mutagenic agents such as UV light, ethane methane sulphonate and N-nitroso-guanidine.

The microorganism produced according to the method of the present invention may be cultivated, in the general microbiological process, on a substrate in which the component from which the monomer units are synthesised is glucose, or a compound metabolisable to glucose. In particular the component is one or more of glucose, fructose, acetate, lactate, ethanol or derivatives thereof.

The present invention may be illustrated with reference to the following examples.

EXAMPLE 1
Induction of Amino Acid Overproduction

*Alcaligenes eutrophus* strain NCIMB 40124 was used as the initial strain which, by a mutation process, gave rise to an amino acid overproducing mutant.

*Alcaligenes eutrophus* NCIMB 40124 was grown on glucose mineral salts medium for approximately 16 hours at 30° C., until an optical density of greater than 1 at 640 $\mu$m was reached.

0.1 ml aliquots were spread on the surface of agar plates containing the same composition but to which had also been added 500 $\mu$m per ml of amino butyric acid. The plates were then incubated for 72 hours at 30° C. Those colonies which had grown were then subcultured, and tested as described below for their ability to produce, and accumulate HV/HB copolymers when provided with a substrate in which the monomer component consisted of glucose.

EXAMPLE 2
Isolation of HV/HB Copolymer Producing Mutants

The subcultures of the colonies for Example 1 were cultivated on typical media which contained sources of nitrogen (ammonium salts), carbon (glucose), and trace elements such as phosphate, sulphate and magnesium. The cultivation was allowed to proceed to nutrient limitation, specifically nitrogen limitation as used in established HB copolymer production. Those cultures which accumulated HV/HB copolymer were regarded as positive. In particular *Alcaligenes eutrophus* strain PS-101 was isolated.

EXAMPLE 3
Production of HV/HB Copolymers

*Alcaligenes eutrophus* strain PS-101 was further cultivated under copolymer accumulating conditions on a medium in which glucose was the sole carbon source.

EXAMPLE 4
Comparative

Example 3 was repeated except that *Alcaligenes eutrophus* strain NCIMB 40124 was used instead of mutant strain PS-101.

Typical results obtained from Examples 3 and 4 are as follows:

|  | % Polymer | |
| --- | --- | --- |
|  | HB | HV |
| NCIMB 40124 | 65 | 0 |
| PS-101 | 55 | 5 |

EXAMPLE 5
Production of Strain NCIMB 40386

Strain NCIMB 40386 was produced from *Alcaligenes eutrophus* strain NCIMB 40124 by the following means:

A single colony of NCIMB 40124 was inoculated into the medium listed in Table 1 containing 1% glucose. The inoculated medium was incubated by shaking at 180 rpm and at a temperature of 28° C. until the mid logarithmic phase. The cells were harvested by centrifugation, washed with 0.85% sodium chloride solution and re-suspended in 0.85% sodium chloride solution and transferred to a glass petri dish. The cells were exposed to UV light to achieve a 99% kill and then inoculated into the medium listed in Table 1 containing 1% glucose. The inoculated medium was incubated by shaking at 180 rpm and at 28° C. for 16 hours in the dark to allow expression of the mutations. The resulting population was spread onto agar plates containing the medium listed in Table 1 and 500 µg/ml α- aminobutyric acid. The plates were incubated for seven days at 28° C. Resistant colonies were selected which showed halos of satellite growth: the halo indicated that the resistant colonies were excreting a substance which relieved the inhibition for the surrounding sensitive cells. This selection produced strain NCIMB 40386 with the ability to produce and accumulate HB/HV copolymer when provided with glucose as shown by Example 6.

TABLE 1

|  | Per Liter Distilled Water |
| --- | --- |
| 0.5 m Phosphate Buffer | 20 ml |
| 36% Ammonium Sulphate | 5 ml |
| 40% Magnesium Sulphate Heptamydrate | 0.5 ml |

TABLE 1-continued

| 0.972% Ferric Chloride | 0.1 ml |
| --- | --- |
| Fisons Trace Elements | 1.0 ml |
| pH 7.0 | |

| Fisons Trace Elements | mg Per Liter Distilled Water |
| --- | --- |
| $Ca^{2+}$ | 720 |
| $Zn^{2+}$ | 22 |
| $Mn^{2+}$ | 25 |
| $Cu^{2+}$ | 5 |
| Counter ion $SO_4^{2-}$ | |

EXAMPLE 6

The growth medium listed in Table 1 containing 1% glucose and 500 µg/ml α- aminobutyric acid was inoculated with a culture of *Alcaligenes eutrophus* NCIMB 40386 produced as described in Example 5. The inoculated medium was shaken using a stirrer speed of 180 rpm and (2") approximately 50 mm (2 inches) throw at a temperature of 28° C. for 24 hours. The cells were harvested by centrifugation, washed with 0.85% sodium chloride solution and then resuspended in the growth medium listed in Table 1 containing 1% glucose and replacing the phosphate buffer with 0.5 m Hepes buffer. The medium was incubated shaking at 180 rpm, (2") approximately 50 mm (2 inches) throw, at a temperature of 28° C. for 48 hours. The cells were harvested by centrifugation, washed with 0.85% sodium chloride solution and freeze dried. The freeze dried cells were ground to a fine powder with a pestle and mortar. 10 g of cells were refluxed with 500 mls chloroform for one hour. The resulting solution was filtered under vacuum and the polymer was recovered by precipitation with methanol and water. The polymer solution was slowly added, with mixing to a solution+consisting of 2 litres water and 500 mls distilled water.

The polymer precipitate was then filtered and dried for 24 hours at 80° C.

Freeze dried cells were prepared for analysis using High Performance Liquid Chromatography (HPLC) by extraction in 55% perchloric acid and neutralised with 20% potassium hydroxide.

Typical HPLC analysis is given below for

|  | % Polymer+ | |
| --- | --- | --- |
|  | HB | HV |
| NCIMB 40124 | 60 | 0 |
| NCIMB 40386 | 45 | 5 |

+Percentage by weight of polymer repeating units based on the total weight of the cells.

EXAMPLE 7
Induction of Amino Acid Overproduction

*Alcaligenes eutrophus* strain H16, a widely available micro-organism available for example from NCIMB as NCIMB 10442 was used as the initial strain in a mutation process which gave rise to amino acid overproducing mutants.

*Algaligenes eutrophus* strain H16 was grown on mineral salts medium containing 1% fructose and the resultant cells subjected to UV mutagenesis by exposure to sufficient UV dose to give between 90 to 99% kill. The survivors were inoculated into nutrient broth (0.8% Oxoid) and were shaken whilst being incubated overnight in the dark at a temperature of 28° C. to allow expression of the mutations.

Following overnight incubation, the colistine technique was used to enrich the population of mutants for auxotrophs. Cells were incubated in the presence of 50 $\mu$g.ml$^{-1}$ colistine for 10 hours. Dilutions of the survivors were plated onto complete medium agar (0.8% nutrient broth and 01.5% NaCl). Replica plating to fructose mineral salts agar (Schlegel H G. Kaltwasser H and Gottschalk G. 1961. Arch. Mikrobiol. 38. 209–222) was used to identify auxotrophic colonies. By this means the mutant *Alcaligenes eutrophus* H16-G131 was isolated. The mutant was found to require isoleucine (Reh M and Schlegel H G. 1969. Arch. Mikrobiol. 67. 99–109).

A mutant, denoted *Alcaligenes eutrophus* H16-R3, which was a spontaneous revertant of H16-G131 to isoleucine prototrophy was isolated by its ability to grow on fructose mineral salts medium. This mutant excretes valine and small amounts of leucine and isoleucine.

EXAMPLE 8
Production of HB/HV Polymers by *Alcaliqenes eutrophus* H16-R3

Colonies of *Alcaligenes eutrophus* H16-R3 were inocculated into 10 mls of nutrient broth (oxoid) and a shake flask preculture was incubated overnight at 30° C. This preculture was then used to inoculate 300 mls of 1% fructose-mineral salts medium containing only 0.05% ammonium chloride in a 1 liter flask. The flask was incubated with shaking at 30° C.

Accumulation of polyhydroxyalkanoate (PHA) started immediately after the ammonium chloride was exhausted. The PHA content of the cells reached 45%. Subsequent analysis of the PHA showed that it consisted of 3-hydroxybutyrate and 3-hydroxyvalerate units, with a 3-hydroxyvalerate content of 4 mole %.

The above described preparation of a HB/HV copolymer was repeated using 1% sodium gluconate as the carbon source. A PHA was produced which on analysis contained 8 mole % of 3-hydroxyvalerate and 92% 3-hydroxybutyrate units.

NCIMB means NCIMB Limited, 23 Machar Drive, Aberdeen, Scotland, UK AB2 1RY. NCIMB 40386 was deposited on Mar. 20, 1991 with NCIMB.

*Alcaligenes eutrophus* H16-R3 is deposited as DSM 6525 with Deutsche Sammlung von Mikroorganismen and Zellkulturen (DSM), Mascheroder Weg 1b, D-3300 Braunschweig, Germany on May 15, 1991.

The taxonomy of *Alkaligenes eutrophus* is given in Bergy's Manual of Systematic Bacteriology, Copyright 1984, Published by Williams and Wilkins.

What is claimed is:

1. A method of producing a microorganism that synthesizes HV/HB copolymer when cultivated on a substrate containing a component, said component being a nutrient from which said microorganism synthesizes both HV and HB monomer units, said method comprising the steps of:
   a) selecting a microorganism that:
      i) metabolizes said substrate to acetyl CoA;
      ii) degrades an amino acid selected from the group consisting of methionine, valine and isoleucine to propionyl CoA;
      iii) synthesizes HB monomer units when cultivated on said substrate;
      iv) polymerizes HB monomer units when cultivated on said substrate; and
      v) does not overproduce said amino acid;
   b) inducing said microorganism to overproduce said amino acid; and
   c) isolating said induced microorganism which accumulates HV/HB copolymer.

2. A method of producing a microorganism that synthesizes HV/HB copolymer when cultivated on a substrate containing a component from which said microorganism synthesizes both HV and HB monomer units, said component being selected from the group consisting of glucose, fructose, an acetate, a lactate, ethanol or a substrate metabolizable thereto, said method comprising the steps of:
   a) selecting a microorganism that:
      i) synthesizes HB monomer units when cultivated on said substrate;
      ii) polymerizes HB monomer units when cultivated on said substrate;
      iii) degrades an amino acid selected from methionine, valine and isoleucine to propionyl CoA; and
      iv) does not overproduce said amino acid;
   b) inducing said microorganism to overproduce said amino acid; and
   c) isolating said induced microorganism which accumulates HV/HB copolymer.

3. The method of claim 1 wherein said microorganism is a strain of Alcaligenes.

4. The method of claim 1 wherein said microorganism is *Alcaligenes eutrophus*.

5. The method of claim 1 wherein overproduction of said amino acid is induced by exposing said microorganism to an amino acid analogue.

6. The method of claim 5 wherein said amino acid analogue is amino butyric acid or norvaline.

7. The method of claim 1 wherein overproduction of said amino acid is induced by a mutation process using ultraviolet light as a mutagenic agent.

8. A method for producing an HV/HB copolymer comprising cultivating the microorganism produced by the method of claim 3 on a substrate comprising glucose, fructose, an acetate, a lactate, ethanol or a chemical metabolizable thereto.

9. *Alcaligenes eutrophus* strain NCIMB 40386, *Alcaligenes eutrophus* strain DSM 6525, and variants and mutants thereof which synthesize HV/HB copolymer when cultivated on a substrate comprising a component from which the microorganism synthesizes both HV and HB monomer units, said component being selected from the group consisting of glucose, fructose, an acetate, a lactate, ethanol and a chemical metabolizable thereto.

* * * * *